(12) United States Patent
Song

(10) Patent No.: US 10,682,121 B2
(45) Date of Patent: Jun. 16, 2020

(54) ULTRASOUND PROBE HAVING ROTATABLE TRANSDUCER ARRAY FOR IMPROVED FIELD OF VIEW AND ULTRASOUND DIAGNOSTIC IMAGING SYSTEM HAVING THE SAME

(71) Applicant: SAMSUNG MEDISON CO., LTD., Hongcheon-gun, Gangwon-do (KR)

(72) Inventor: In Seong Song, Daegu (KR)

(73) Assignee: Samsung Medison Co., Ltd., Hongcheon-Gun, Gangwon-Do (KR)

( * ) Notice: Subject to any disclaimer, the term of this patent is extended or adjusted under 35 U.S.C. 154(b) by 716 days.

(21) Appl. No.: 14/959,977

(22) Filed: Dec. 4, 2015

(65) Prior Publication Data

US 2016/0157819 A1    Jun. 9, 2016

(30) Foreign Application Priority Data

Dec. 5, 2014 (KR) ........................ 10-2014-0173559

(51) Int. Cl.
*A61B 8/00* (2006.01)
*A61B 8/12* (2006.01)

(52) U.S. Cl.
CPC .............. *A61B 8/4461* (2013.01); *A61B 8/12* (2013.01); *A61B 8/44* (2013.01); *A61B 8/4405* (2013.01); *A61B 8/4483* (2013.01); *A61B 8/461* (2013.01)

(58) Field of Classification Search
None
See application file for complete search history.

(56) References Cited

U.S. PATENT DOCUMENTS

| 5,662,116 A | 9/1997 | Kondo et al. |
| 6,102,860 A * | 8/2000 | Mooney ............ A61B 8/08 128/916 |
| 2006/0074316 A1 | 4/2006 | Kadokura |
| 2007/0016060 A1 | 1/2007 | Hwang |
| 2011/0037348 A1 * | 2/2011 | Sakamoto ............ F16C 29/04 310/323.02 |
| 2011/0071398 A1 * | 3/2011 | Hwang ............ A61B 8/12 600/459 |

(Continued)

FOREIGN PATENT DOCUMENTS

| CN | 1720006 A | 1/2006 |
| CN | 106659476 A | 5/2017 |

(Continued)

OTHER PUBLICATIONS

Extended European Search Report dated May 6, 2016 issued in European Patent Application No. 15192989.0.

(Continued)

*Primary Examiner* — Angela M Hoffa
*Assistant Examiner* — Farouk A Bruce
(74) *Attorney, Agent, or Firm* — Morgan, Lewis & Bockius LLP

(57) ABSTRACT

An ultrasound probe having a rotatable transducer array for providing an improved field of view (FOV) and an improved scan angle includes a transducer comprising a transducer array and rotating at a predetermined angle. A supporting member supports the transducer and includes a rotation guide which is in contact with the transducer while the transducer rotates.

17 Claims, 24 Drawing Sheets

(56) References Cited

U.S. PATENT DOCUMENTS

| | | | |
|---|---|---|---|
| 2011/0201937 A1* | 8/2011 | Fujii | A61B 8/14 600/459 |
| 2012/0143063 A1* | 6/2012 | Robinson | A61B 8/00 600/472 |
| 2013/0123577 A1* | 5/2013 | Ho | A61B 1/00006 600/109 |
| 2013/0172751 A1 | 7/2013 | Heinrich et al. | |
| 2017/0258447 A1* | 9/2017 | Lee | A61B 8/4461 |

FOREIGN PATENT DOCUMENTS

| | | |
|---|---|---|
| EP | 1744178 A2 | 1/2007 |
| JP | 2003-038489 | 2/2003 |
| WO | 2006119173 A1 | 11/2006 |
| WO | 2012076918 A1 | 6/2012 |

OTHER PUBLICATIONS

Chinese Office Action dated Sep. 3, 2019 issued in Chinese Patent Application No. 201510883170.3 (with English translation).
Office Action issued in corresponding European Application No. 15 192 989.0, dated Jun. 4, 2019.

\* cited by examiner

-PRIOR ART-

-PRIOR ART-

ULTRASOUND PROBE HAVING ROTATABLE TRANSDUCER ARRAY FOR IMPROVED FIELD OF VIEW AND ULTRASOUND DIAGNOSTIC IMAGING SYSTEM HAVING THE SAME

CROSS-REFERENCE TO RELATED APPLICATION

This application claims the benefit of priority to Korean Patent Application No. 10-2014-0173559, filed on Dec. 5, 2014 in the Korean Intellectual Property Office, the disclosure of which is incorporated herein by reference.

TECHNICAL FIELD

The present disclosure relates to an ultrasound probe having a rotatable transducer array, which can provide an improved field of view (FOV) and an improved scan angle, and an ultrasound diagnostic imaging system having the ultrasound probe

BACKGROUND

An ultrasound diagnostic imaging system transmits ultrasonic signals to a target region of an object from a surface of the object and receives ultrasonic signals (ultrasonic echo signals) reflected from the target region to non-invasively acquire slice images about soft tissue of the object or images about blood vessels of the object based on the received ultrasonic signals.

The ultrasound diagnostic imaging system is a compact, low-priced apparatus and displays the images in real time, compared to other medical imaging systems, such as an X-ray diagnostic system, an X-ray computerized tomography (CT) scanner, a magnetic resonance image (MRI) system, and a nuclear medical diagnostic system. Further, the ultrasound diagnostic system improves safety performance since patients are not exposed to radiation such as X-rays. Accordingly, the ultrasound diagnostic system is widely used to diagnose heart, abdomen, urinary organs, uterus, etc.

The ultrasound diagnostic system includes an ultrasound probe to transmit ultrasound signals to the object to obtain ultrasound images of the object and to receive the ultrasonic signals reflected from the object.

The ultrasound probe includes a piezoelectric layer to convert electrical signals into acoustic signals or acoustic signals into electrical signals according to vibration of a piezoelectric material. A matching layer reduces a difference in acoustic impedance between the probe and the object so that ultrasonic waves generated by the probe can be transferred to the object. A lens layer focuses the ultrasonic waves which move forward from the transducer on a specific region. A backing layer blocks the ultrasonic waves from transmitting backward from the transducer to prevent image distortion.

SUMMARY

An aspect of the present inventive concept provides an ultrasound probe having improved field of view (FOV) and scan angle, and an ultrasound diagnostic imaging system having the ultrasound probe.

Additional aspects of the inventive concept will be set forth in part in the description which follows and, in part, will be obvious from the description, or may be learned by practice of the disclosure.

In accordance with an embodiment of the present inventive concept, an ultrasound probe includes a transducer including a transducer array and rotating at a predetermined angle. A supporting member supports the transducer while the transducer rotates.

The supporting member may include a rotation guide, which is in contact with the transducer module, having a shape corresponding to the shape of the transducer module while the transducer rotates.

The supporting member may include at least one of a roller and a bearing which is in contact with the transducer.

The ultrasound probe may further include a wire member transferring power for rotating the transducer to the transducer. The transducer may include an installation groove in which the wire member is inserted.

The supporting member may include a rotation guide which is in contact with the installation groove of the transducer and guiding the installation groove while the transducer rotates.

The transducer array may extend perpendicular to a direction in which the transducer rotates.

The ultrasound probe may have a field of view (FOV) of 150 degrees or more.

The transducer may have a rotational angle of 180 degrees or more.

In accordance with another embodiment of the present inventive concept, an ultrasound probe includes a transducer comprising a transducer array and rotating at a predetermined angle. At least one supporting member is inserted into the inside of the transducer to support the transducer and coupled with the transducer inside the transducer while the transducer rotates.

The transducer may include at least one installation groove into which the at least one supporting member is inserted.

The at least one groove may have a fan shape and have a central angle of 180 degrees or more.

The ultrasound probe may further include a wire member transferring power for rotating the transducer to the transducer. The transducer may include an installation groove in which the wire member is inserted.

The transducer array may extend perpendicular to a direction in which the transducer rotates.

The ultrasound probe may have an FOV of 150 degrees or more.

The transducer may have a rotational angle of 180 degrees or more.

In accordance with further another embodiment of the present inventive concept, an ultrasound diagnostic imaging system includes an ultrasound probe transmitting ultrasound waves to an object, receiving ultrasonic waves reflected from the object, and converting the reflected ultrasonic waves into electrical signals. A main body connected to the ultrasound probe through a cable and including an input and a display. The ultrasound probe includes: a transducer comprising a transducer array and rotating at a predetermined angle; and a supporting member supporting the transducer while the transducer rotates on the supporting member.

BRIEF DESCRIPTION OF THE DRAWINGS

These and/or other aspects of the inventive concept will become apparent and more readily appreciated from the following description of the embodiments, taken in conjunction with the accompanying drawings.

DETAILED DESCRIPTION

Figure 1:
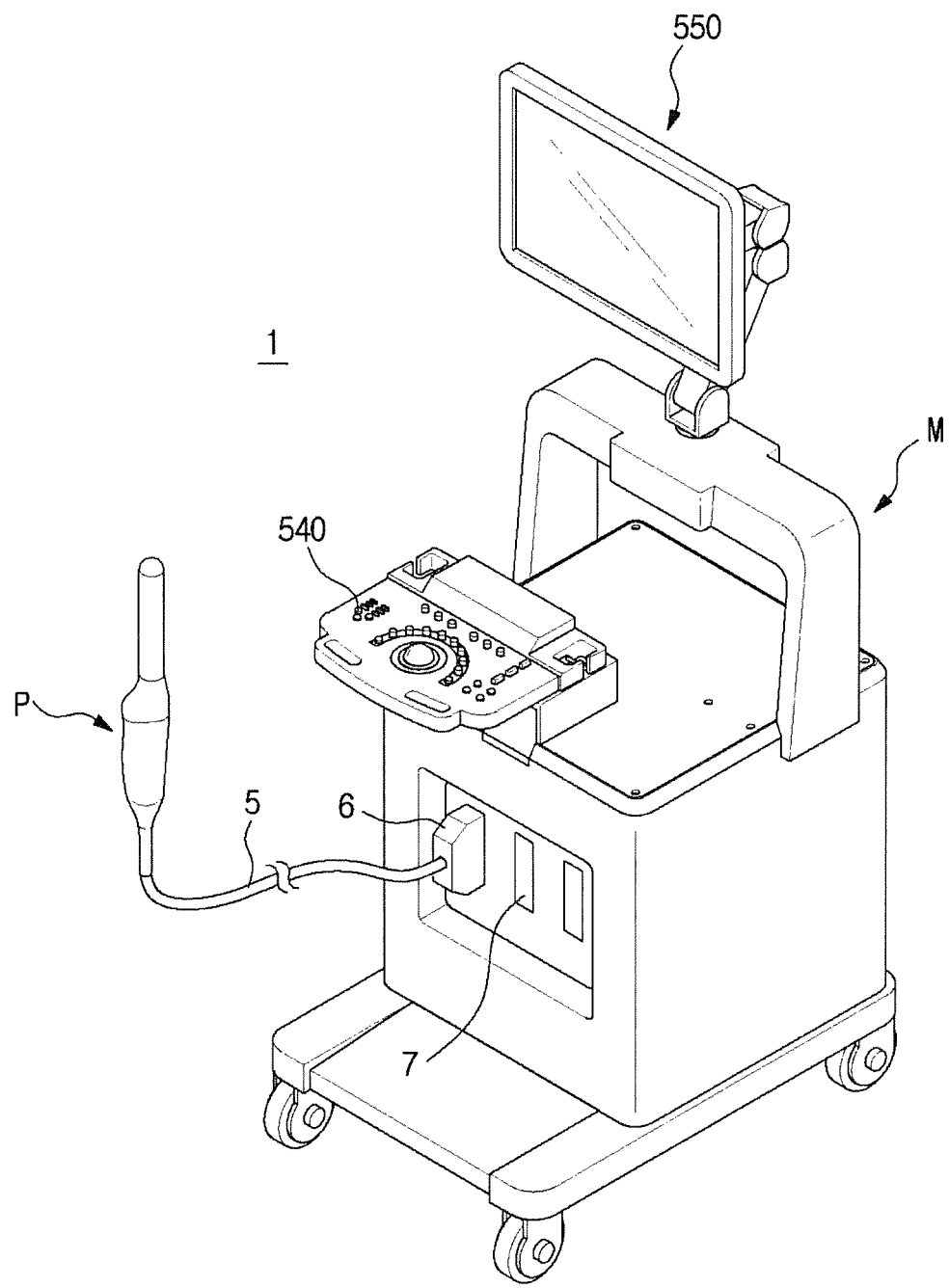
FIG. 1 illustrates an external appearance of an ultrasound diagnostic imaging system according to an embodiment of the present inventive concept.

Reference will now be made in detail to the embodiments of the present inventive concept, examples of which are illustrated in the accompanying drawings, wherein like reference numerals refer to like elements throughout.

FIG. 1 illustrates an external appearance of an ultrasound diagnostic imaging system according to an embodiment of the present inventive concept.

Referring to FIG. 1, an ultrasound diagnostic imaging system 1 may include an ultrasound probe "P" transmitting ultrasonic waves to an object, receiving ultrasonic waves reflected from the object, and converting the reflected ultrasonic waves into electrical signals. A main body M, which is connected to the ultrasound probe "P", includes an input 540 and a display 550, and displays ultrasound images.

The ultrasound probe "P" may be connected to the main body M of the ultrasound diagnostic imaging system 1 through a cable 5 to receive various signals for controlling the ultrasound probe "P" from the main body M or to transfer analog or digital signals corresponding to ultrasound echo signals received by the ultrasound probe "P" to the main body M.

The ultrasound probe "P" may be a wireless probe that receive and transmit signals from and to the main body M through a network established between the ultrasound probe "P" and the main body M.

One end of the cable 5 may be connected to the ultrasound probe "P", and another end of the cable 5 may include a connector 6 detachably inserted into at least one of slots 7 formed in the main body M. The main body M and the ultrasound probe "P" may exchange control commands or data through the cable 5.

For example, if a user inputs information about a focal depth, the size or shape of aperture, a steering angle, etc. through the input 540, the information may be transferred to the ultrasound probe "P" through the cable 5 and used for transmission and reception beamforming.

When the ultrasound probe "P" is a wireless probe, it can exchange control commands or data with the main body M through a wireless network without the cable 5.

The input 540 may allow the user to input commands for operations of the ultrasound diagnostic imaging system 1. The user may input an ultrasonic diagnosis start command, a diagnosis mode selection command for selecting a diagnosis mode, such as an amplitude mode (A-mode), a brightness mode (B-mode), a color flow mode (C-mode), a Doppler mode (D-mode), and a motion mode (M-mode), or region of interest (ROI) setting information including a size and a location of ROI, through the input 540.

The input 540 may include various means, such as a keyboard, a mouse, a trackball, a tablet, or a touch screen module for the user to input data, instructions, or commands.

The display 550 may display menus or guidance needed for ultrasonic diagnosis, and ultrasound images obtained during the ultrasonic diagnosis. The display 550 may display ultrasound images about a target region inside the object, created by an image processor (not shown). An ultrasound image displayed on the display 550 may be an A-mode ultrasound image, a B-mode ultrasound image, or a 3-dimensional (3D) ultrasound image. The display 550 may be one of various displays, such as a cathode ray tube (CRT) and a liquid crystal display (LCD).

Figure 2:
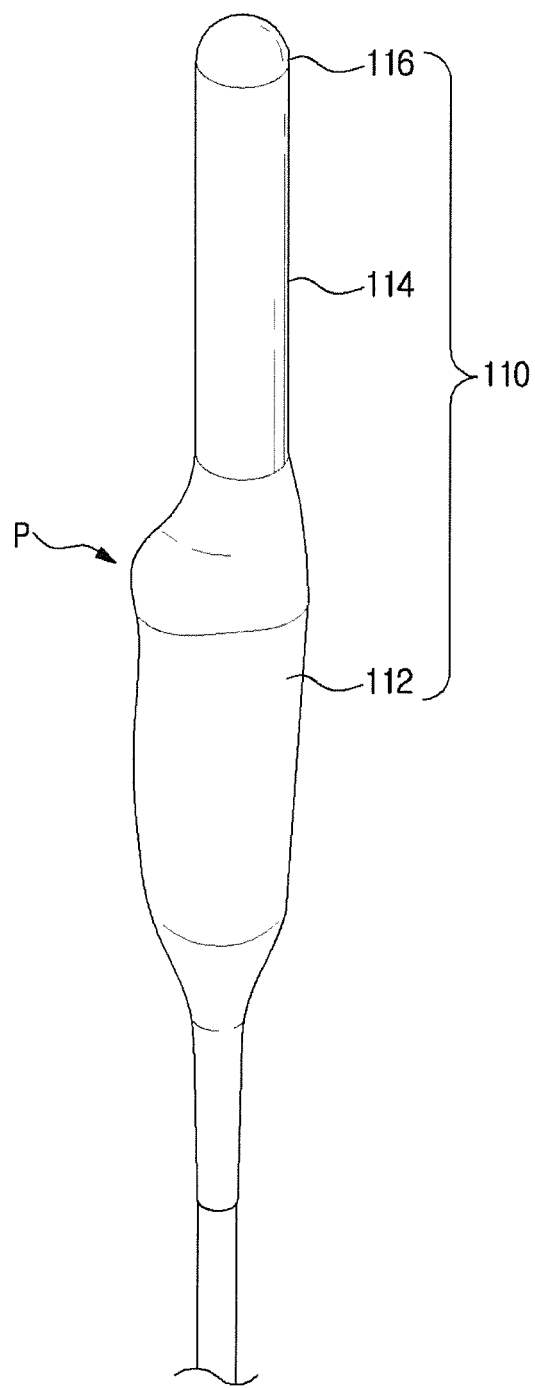
FIG. 2 illustrates an external appearance of an ultrasound probe according to an embodiment of the present inventive concept.
Figure 3:
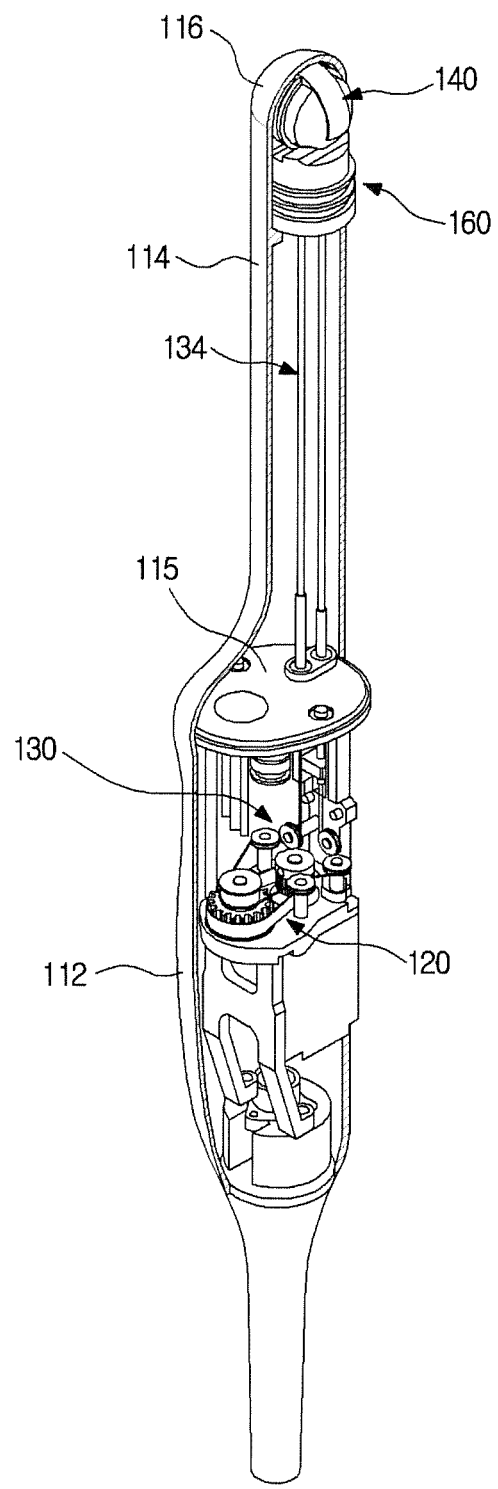
FIG. 3 is a perspective view showing a cross section of an internal structure of the ultrasound probe according to an embodiment of the present inventive concept.
Figure 4:
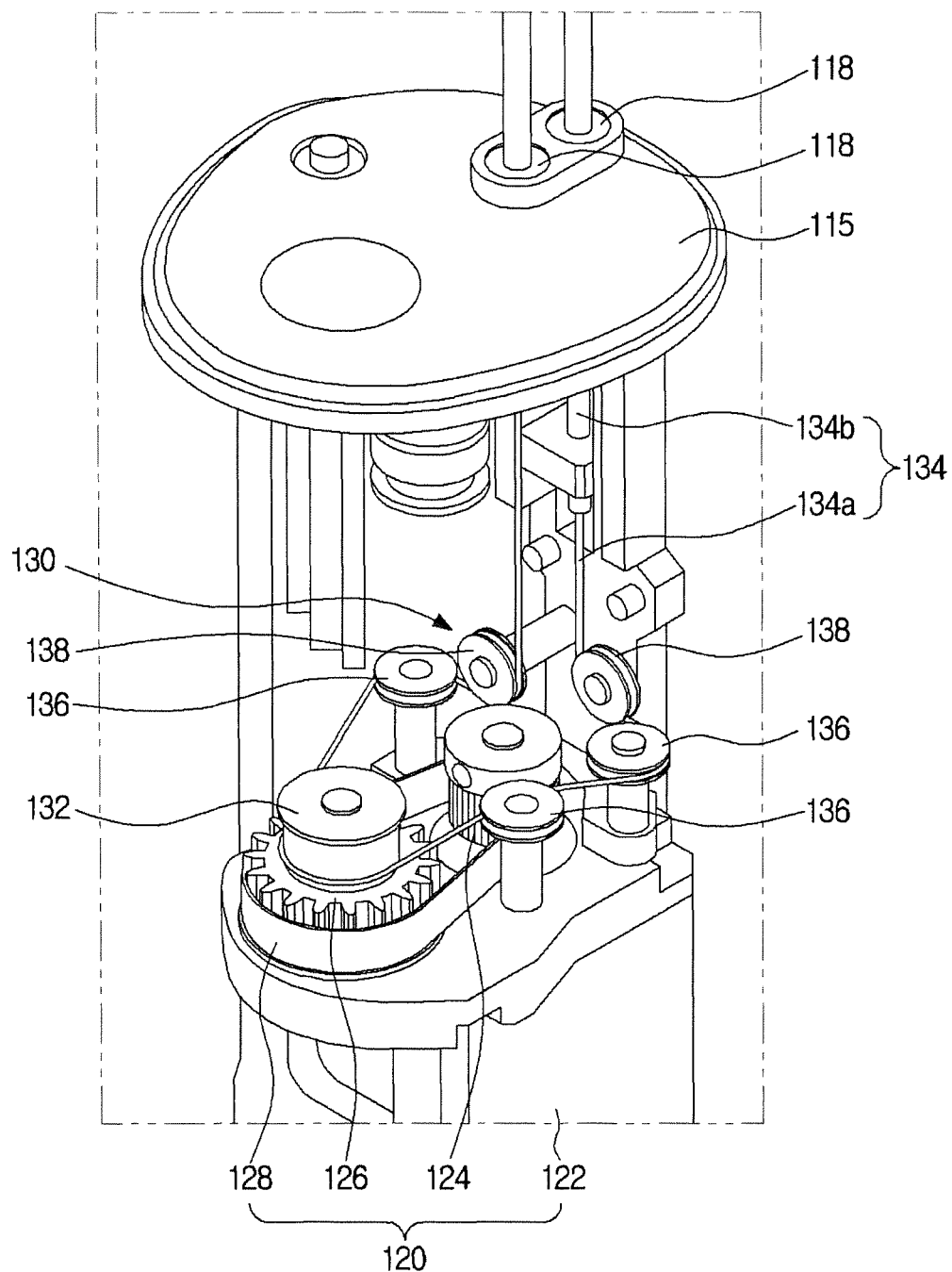
FIG. 4 is an enlarged view showing an internal structure of a lower housing of FIG. 2.

FIG. 2 illustrates an external appearance of an ultrasound probe according to an embodiment of the present inventive concept, FIG. 3 is perspective view showing a cross section of an internal structure of the ultrasound probe according to an embodiment of the present inventive concept, and FIG. 4 is an enlarged view showing an internal structure of a lower housing of FIG. 2.

Referring to FIG. 2, a housing 110 of the ultrasound probe "P" according to the present disclosure may include a lower housing 112, a upper housing 114, and a cover housing 116.

The lower housing 112 may include a driver 120 for driving the ultrasound probe "P" therein (see FIG. 3).

The driver 120 may generate power in a forward or backward direction. Referring to FIG. 4, the driver 120 may include a driving motor 122, a driving pulley 124, a middle pulley 126, and a belt member 128.

The driving motor 122 may generate rotatory power in a forward or backward direction.

The driving pulley 124 may be shaft-coupled with the driving motor 122. The driving pulley 124 may receive the power from the driving motor 122, and rotate in a forward or backward direction by the rotatory power generated by the driving motor 122.

The middle pulley 126 may be spaced apart from the driving pulley 124. The middle pulley 126 may be rotatably installed, and receive the power from the driving pulley 124 through the belt member 128 that transfers the power from the driving pulley 124 to the middle pulley 126.

A power transmitter 130 may be linked with the driver 120 to transfer the power. The power transmitter 130 may be installed in the lower housing 112 and the upper housing 114. The power transmitter 130 may include a power transfer pulley 132, a wire member 134, a first guide pulley 136, and a second guide pulley 138.

The power transfer pulley 132 may receive the power from the driver 120. In the exemplary embodiment, the power transfer pulley 132 may be coupled with the same shaft with which the middle pulley 126 is coupled, and rotates by rotation of the middle pulley 126, thereby receiving the power from the driver 120. The power transfer pulley 132 may rotate in the forward or backward direction according to the rotation of the middle pulley 126.

The wire member 134 may connect the power transfer pulley 132 to a transducer 140. The wire member 134 may include a wire 134a and a pin rod 134b.

The wire 134a may connect the power transfer pulley 132 to the transducer 140, in which one end of the wire 134a may be connected to the power transfer pulley 132, and another end of the wire 134a may be connected to the transducer 140. In the exemplary embodiment, the wire 134a may penetrate a partition wall 115 through one or more through holes formed in the partition wall 115. The wire 134a may wind around or unwind from the power transfer pulley 132 by the forward or backward rotation of the power transfer pulley 132 to move the transducer 140.

The pin rod 134b may be fixed around a middle portion of the wire 134a, and move together with the wire 134a. The pin rod 134b may be inserted into the through holes of the partition wall 115 and have a sufficient length to be fixed in the through holes when moving together with the wire 134a.

In the exemplary embodiment, one or more oil seals 118 may be attached along inner sides of the through holes, which are in contact with the pin rod 134b, to tightly contact the pin rods 134b. The tight contact of the pin rod 134b and the one or more oil seals 118 may seal the though holes to prevent oil contained in the upper housing 114 from leaking out through the through holes.

The first guide pulley 136 may guide a first direction movement of the wire member 134 connected to the power transfer pulley 132. The first guide pulley 136 may be spaced apart from and rotate in the same direction as the power transfer pulley 132. In the exemplary embodiment, the first direction may be tangential to the rotation of the power transfer pulley 132.

The second guide pulley 138 may be installed in a different direction from the first guide member 136, and guide a second direction movement of the wire member 134. The second guide pulley 138 may be spaced apart from and rotate in a direction that is vertical to a rotation direction of the first guide pulley 136. In the exemplary embodiment, the second direction may be vertical to the first direction.

The wire member 134, which winds or unwinds as the power transfer pulley 132 rotates, may move in the second direction by the second guide pulley 138 to move the transducer 140.

The upper housing 114 may be installed above the upper housing 112, and accommodate the transducer 140 therein. The oil may be contained in the upper housing 114 such that the transducer 140 sinks under the oil inside the upper housing 114. The partition wall 115 may be disposed between the lower housing 112 and the upper housing 114 and partition the lower housing 112 and the upper housing 114 to prevent the oil from leaking to inside the lower hosing 112.

The cover housing 116 may be attached to one end of the upper housing 114. The cover housing 116 may contact an object, and accommodate the transducer 140 together with the upper housing 114.

Figure 5:
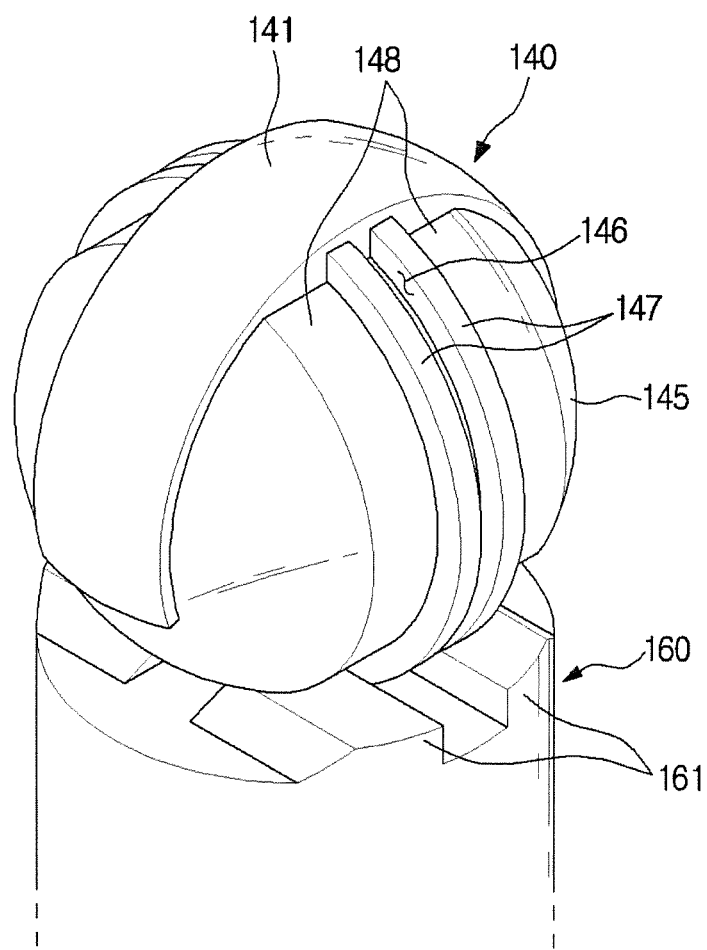
FIG. 5 is a perspective view of a transducer and a supporting member, according to a first embodiment of the present inventive concept.
Figure 6A:
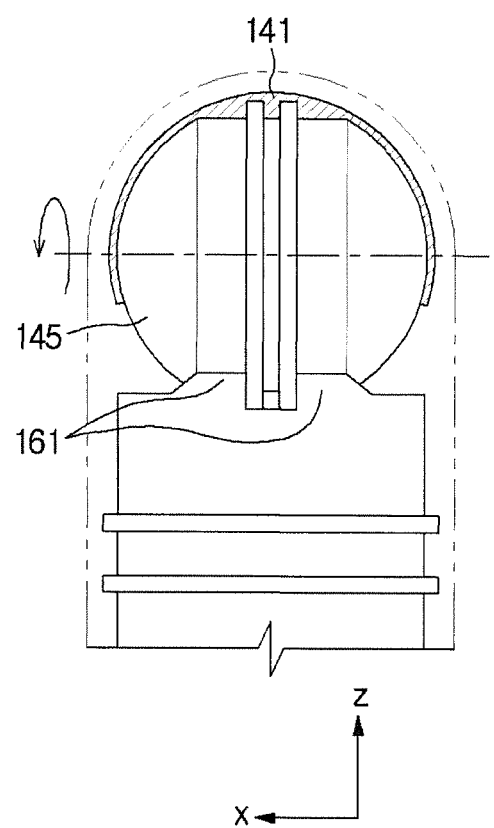
FIGS. 6A and 6B illustrate the transducer and the supporting member, according to the first embodiment of the present inventive concept.
Figure 6B:
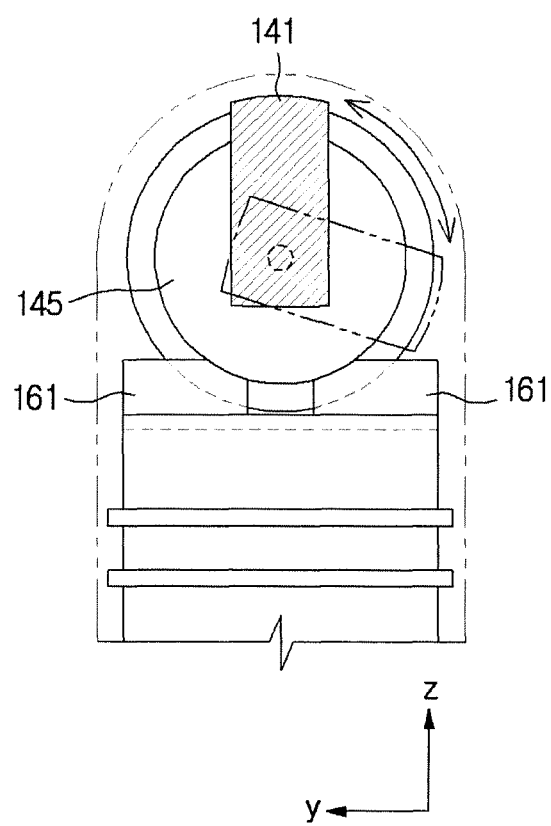
Figure 7A:
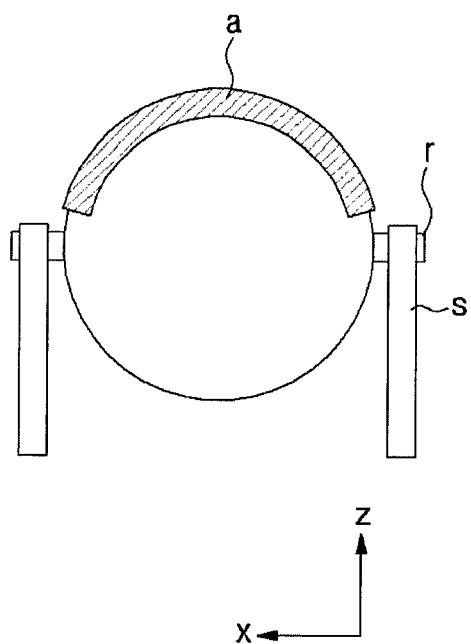
FIGS. 7A and 7B show a transducer with a rotating shaft extending to the outside.
Figure 7B:
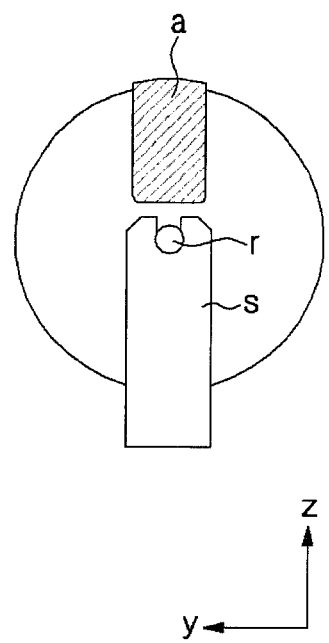

FIG. 5 is a perspective view of a transducer and a supporting member, according to a first embodiment of the present inventive concept, FIGS. 6A and 6B illustrates the transducer and the supporting member, according to the first embodiment of the present inventive concept, and FIGS. 7A and 7B show a transducer with a rotating shaft extending to outside.

Referring to FIGS. 5 to 6B, the transducer 140 of the ultrasound probe "P" according to the present disclosure may include a transducer array 141 to generate ultrasonic waves, and a globe-shaped base 145 on which the transducer array 141 is installed. The ultrasound probe "P" has a supporting member 160 corresponding to the shape of the transducer 140 below the transducer 140 to support and allow rotation of the transducer 140.

Each transducer 140 having the transducer array 141 may be a magnetostrictive ultrasonic transducer using the magnetostrictive effect of a magnetic material, a capacitive micromachined ultrasonic transducer (CMUT) that transmits and receives ultrasonic waves using vibration of several hundreds or thousands of micromachined thin films, or a piezoelectric ultrasonic transducer using the piezoelectric effect of a piezoelectric material. In the following description, the transducer 140 is a piezoelectric ultrasound transducer.

A phenomenon in which a voltage is generated when a mechanical pressure is applied to a specific material is called a piezoelectric effect, and a phenomenon in which mechanical deformation occurs when a voltage is applied to a specific material is called a converse piezoelectric effect. Materials having the piezoelectric effect and converse piezoelectric effect are piezoelectric materials. That is, the piezoelectric materials can convert electrical energy into mechanical vibration energy or vice versa.

The ultrasound probe "P" may include the transducer array 141 made of a piezoelectric material that converts electrical signals into mechanical vibrations to generate ultrasonic waves. The piezoelectric material constituting the transducer array 141 may be a ceramic of lead zirconate titanate (PZT), a solid solution of lead magnesium niobate and lead titanate (PZMT) of a single crystal, or a solid solution of lead zincniobate and lead titanate of a single crystal (PZNT). The transducer array 141 may be a 1-dimensional (1D) or 2-dimensional (2D) array. Since the ultrasound probe "P" can obtained 3D images by mechanically rotating the transducer array 141, the transducer array 141 may be the 1D array.

Since the ultrasound probe "P" obtains volume data of an object by transmitting and receiving the ultrasonic waves while rotating the transducer array 141, the globe-shaped base 145 on which transducer array 141 is installed may have a rotatable shape so that the transducer array 141 can rotate. As shown in FIGS. 5 to 6B, the base 145 may have a globe shape or a nearly-globe shape although it may deviate from a perfect globe during a manufacturing process. The transducer array 141 may be disposed around a front portion of the base 145. Since the base 145 has the globe shape, the transducer array 141 disposed around the base 145 may have a curved surface. The ultrasound probe "P"

includes a fixed shaft extending out of the base 145 for rotating the transducer 140, and thus, the transducer array 141 having a relatively large size can be disposed around the base 145, as shown in FIGS. 5 to 6B. Referring to FIGS. 7A and 7B, since the transducer array 141 extends at right angles toward a direction in which the base 145 rotates, when a rotating shaft "r" extends out of the base 145 and a supporting member "S" supports the rotating shaft "r", a size of the transducer array 141 is limited by the rotating shaft "r". That is, if the size "a" of the transducer array 141 exceeds a reference size, the transducer array 141 will collide with the rotating shaft "r". The ultrasound probe "P" including the transducer 140 as shown in FIGS. 7A and 7B cannot have an FOV that is greater than 180 degrees due to the limitation in the transducer array size "a". Accordingly, the ultrasound probe "P" has an FOV of about 150 degrees.

However, since the transducer 140 according to the present disclosure as shown in FIGS. 5 to 6B includes a fixed shaft extending out of the base 145, the transducer array 141 can have a relatively large size. Accordingly, the ultrasound probe "P" according to the present disclosure may have an FOV that is greater than 180 degrees, thereby obtaining 3D volume data for a relatively wider scan area.

The supporting member 160 may have, as shown in FIGS. 5 to 6B, one or more curved surfaces corresponding to the curved surface of the base 145 in order to support the base 145 and to guide the rotation of the base 145 while contacting the base 145. The curved surfaces of the supporting member 160 are referred to as rotation guides 161.

The base 145 may be supported by the supporting member 160, and rotate on the supporting member 160 by power applied from the driver 120 (see FIG. 3) to the base 145. As shown in FIG. 5, the base 145 may include an installation groove 146 in which the wire member 143 is installed. The installation groove 146 may be space formed between two protrusions 147. Along both sides of the installation groove 146, contact surfaces 148 may contact the rotation guides 161 of the supporting member 160. When the power is transferred to the base 145 through the wire member 134, the contact surfaces 148 of the base 145 may rotate in a clockwise or counterclockwise direction along the rotation guides 161 while contacting the rotation guides 161, so that the base 145 rotates.

Hereinafter, various structures of the supporting member 160 and the rotation of the transducer 140 according to the various structures of the supporting member 160 will be described in more detail.

Figure 8A:
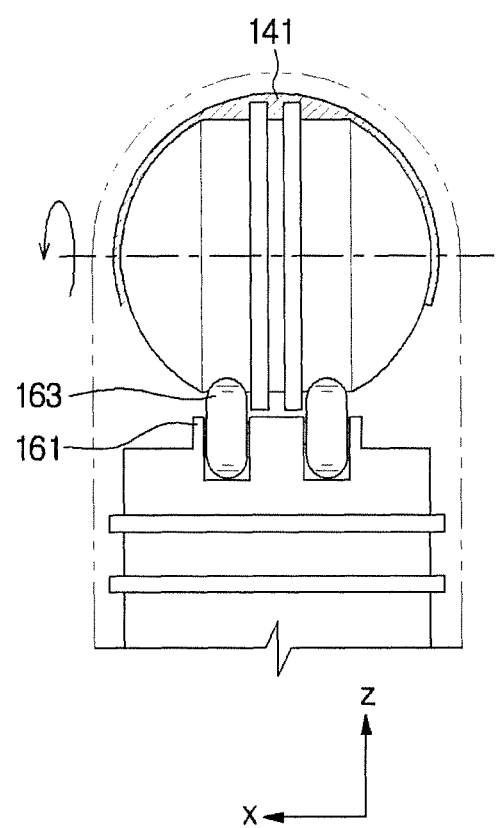
FIGS. 8A and 8B illustrate a transducer and a supporting member, according to a second embodiment of the present inventive concept.
Figure 8B:
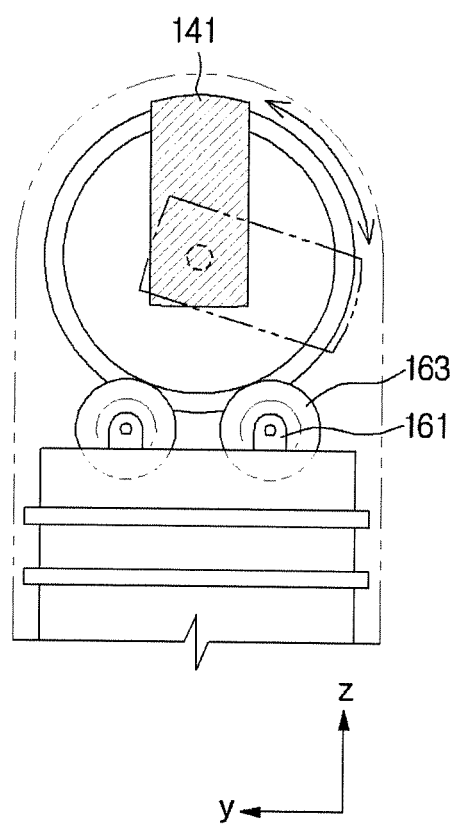

FIGS. 8A and 8B illustrate a transducer and a supporting member, according to a second embodiment of the present inventive concept. According to the second embodiment, the supporting member 160 may further include one or more friction reducers 163, such as bearings or rollers, in order to reduce friction forces between the contact surfaces 148 of the base 145 and the rotation guides 161. Therefore, the base 145 can rotate more smoothly with less power.

However, the friction reducers 163 may be, instead of bearings and rollers, any other structure that can reduce friction forces between the rotation guides 161 and the contact surfaces 148. The shape or number of the friction reducers 163 shown in FIGS. 8A and 8B are exemplary, and are not limited thereto.

Figure 9:
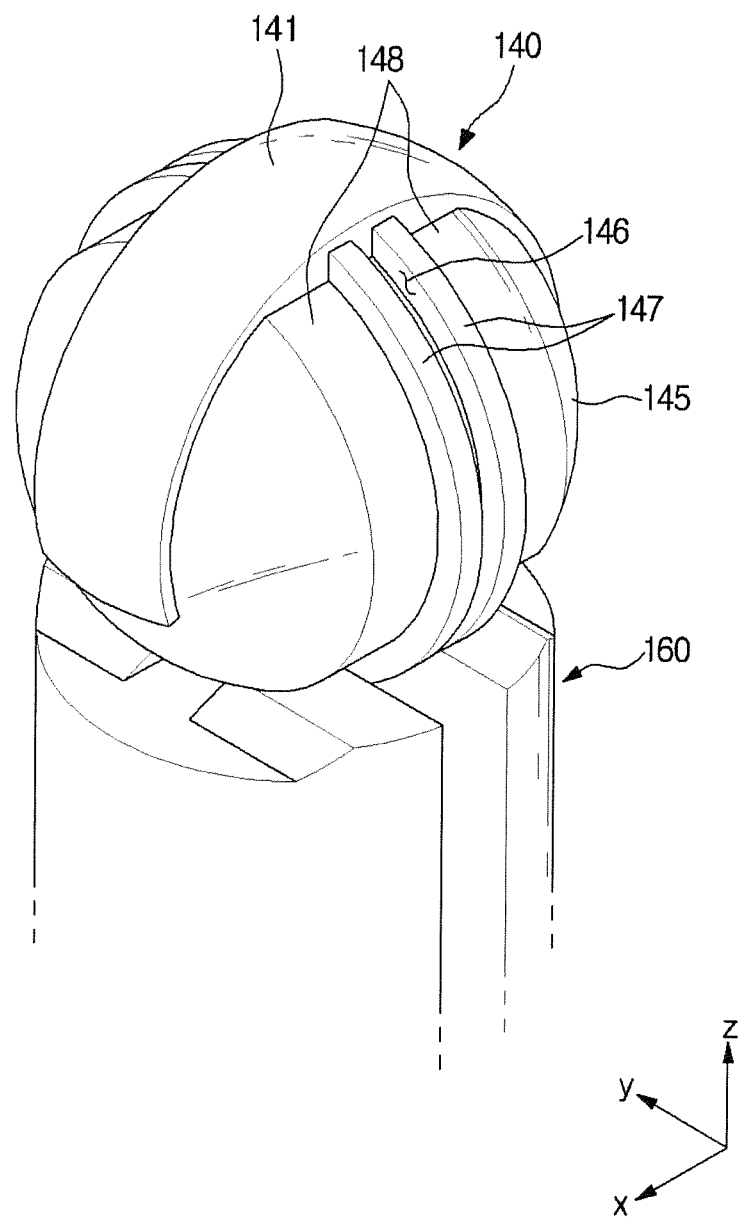
FIG. 9 is a perspective view of a transducer and a supporting member, according to a third embodiment of the present inventive concept.
Figure 10A:
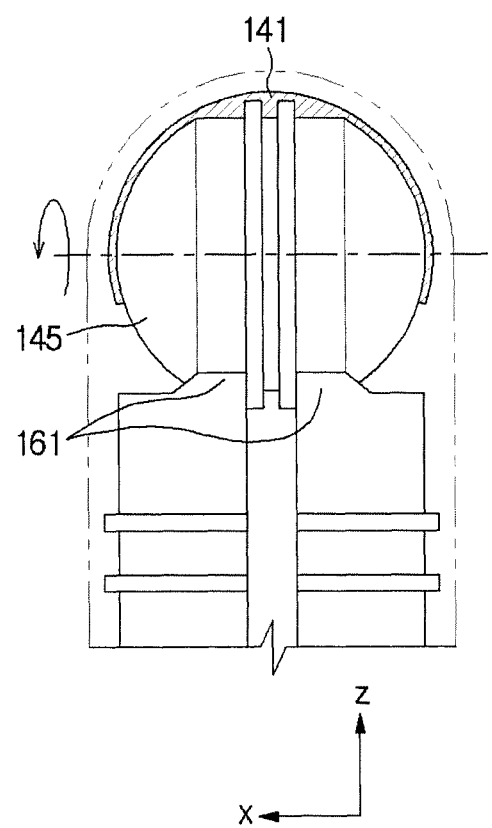
FIGS. 10A and 10B illustrate the transducer and the supporting member, according to the third embodiment of the present inventive concept.
Figure 10B:
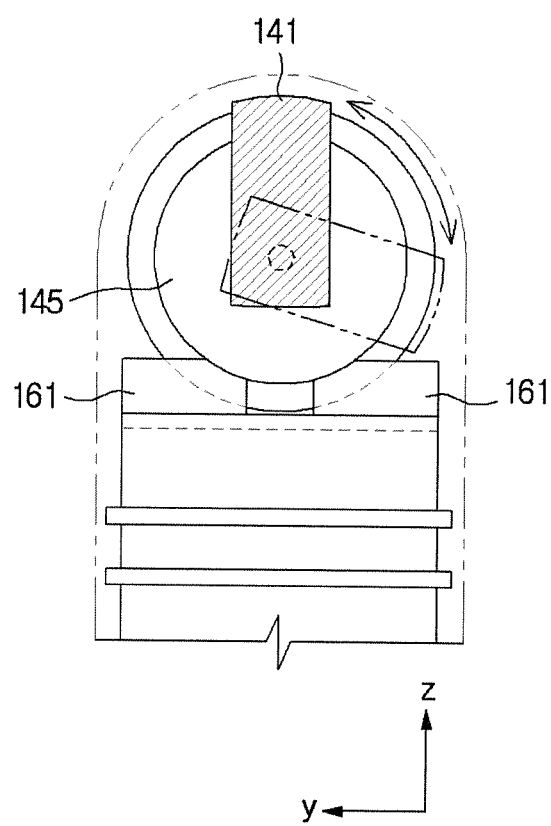

FIG. 9 is a perspective view of a transducer and a supporting member, according to a third embodiment of the present inventive concept, and FIGS. 10A and 10B illustrate the transducer and the supporting member, according to the third embodiment of the present inventive concept.

According to the third embodiment, the supporting members 160 may be configured with two separated bodies unlike the supporting member 160 according to the first embodiment formed as one body as shown in FIG. 5. The supporting members 160 may have, as shown in FIGS. 9 to 10B, curved surfaces corresponding to the curved surfaces 148 of the base 145, in order to support the base 145 and guide rotation of the base 145 while contacting the base 145. The curved surfaces of the supporting members 160 are referred to as rotation guides 161.

The base 145 may be supported by the supporting members 160, and rotate on the supporting members 160 by the power applied from the driver 120 (see FIG. 3) to the base 145. As shown in FIG. 9, the base 145 may include an installation groove 146 in which the wire member 134 is installed. The installation groove 146 may be a space between two protrusions 147. Along both sides of the installation groove 146, the contact surfaces 148 may contact the rotation guides 161 of the supporting members 160. When the power is transferred to the base 145 through the wire member 134, the contact surfaces 148 of the base 145 may rotate in a clockwise or counterclockwise direction along the rotation guides 161 of the supporting members 160 while contacting the rotation guides 161, so that the base 15 rotates. Although not shown in FIGS. 9 to 10B, one or more friction reducers 163, such as bearings or rollers, may be respectively installed in the supporting members 160 similar to the second embodiment (see FIGS. 8A and 8B). That is, the two supporting members 160 may further include one or more friction reducers 163, such as bearings or rollers, in order to reduce friction forces between the rotation guides 161 and the contact surfaces 148 of the base 145. Thus, the base 145 can rotate more smoothly with less power.

However, the friction reducers 163 may be, instead of bearings and rollers, any other structure that can reduce friction forces between the rotation guides 161 of the supporting member 160 and the contact surfaces 148 of the base 145. The rotation guides 161 of the supporting member (s) 160 according to the first to third embodiments may be made of a low friction material, or the surfaces of the rotation guides 161 may be coated with a low friction material, in order to reduce friction forces with the contact surfaces 148 of the base 145.

Figure 11A:
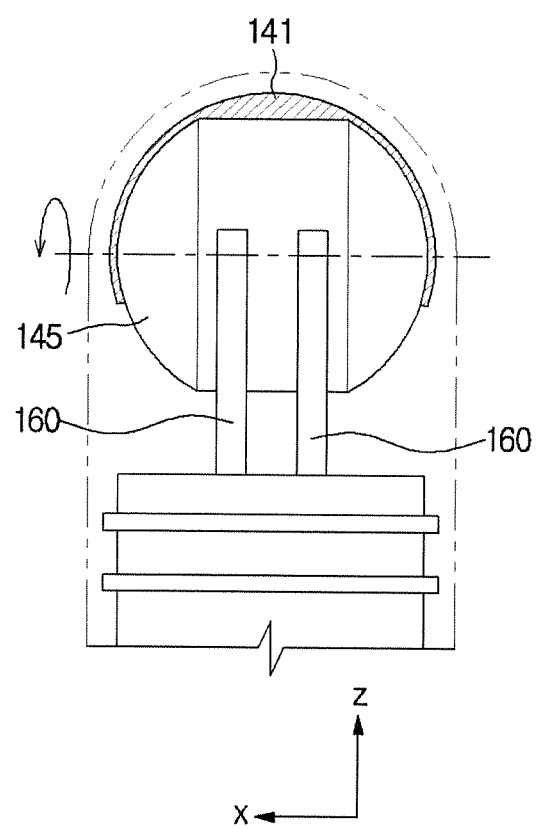
FIGS. 11A and 11B illustrate a transducer and a supporting member, according to a fourth embodiment of the present inventive concept.
Figure 11B:
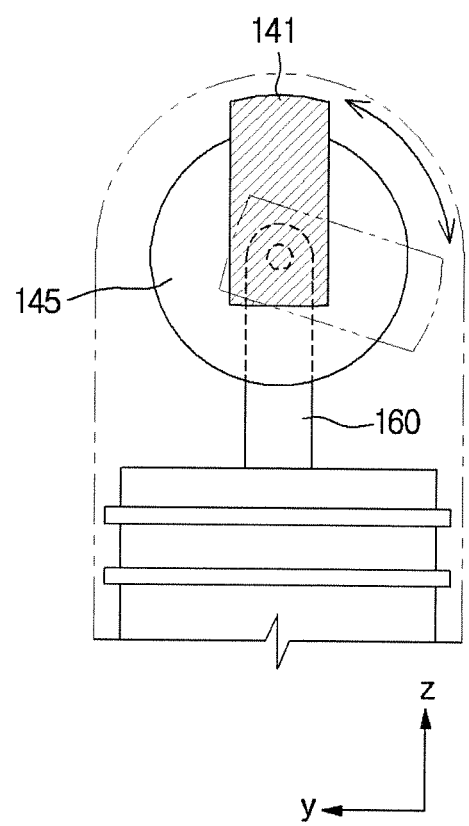
Figure 12A:
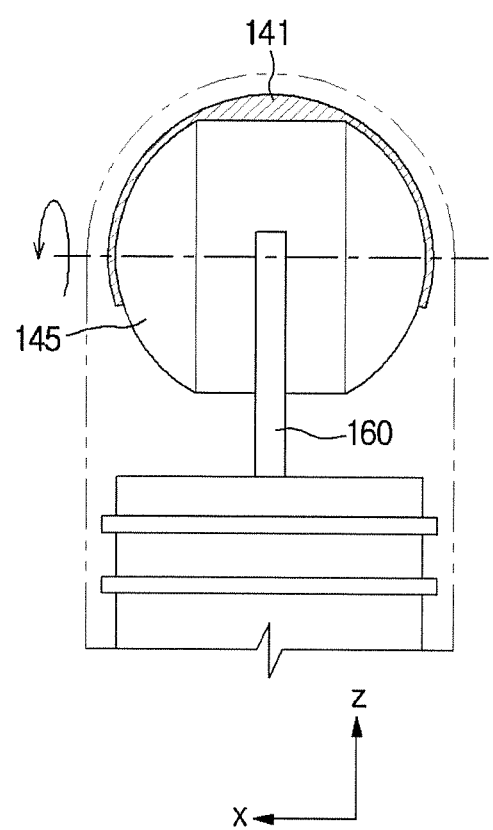
FIGS. 12A and 12B illustrate a transducer and a supporting member, according to a fifth embodiment of the present inventive concept.
Figure 12B:
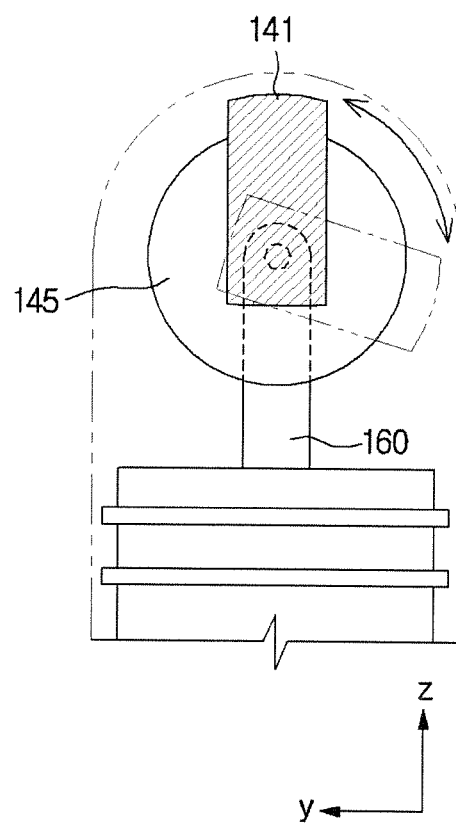

FIGS. 11A and 11B illustrate a transducer and a supporting member, according to a fourth embodiment of the present disclosure, and FIGS. 12A and 12B illustrate a transducer and a supporting member, according to a fifth embodiment of the present inventive concept.

As shown in FIGS. 11A and 11B, the supporting member 160 according to a fourth embodiment of the present inventive concept may be partially inserted into the transducer 140. The base 145 may include an installation groove 146 into which the supporting member 160 is inserted. The supporting member 160 that is inserted into the installation groove 146 may have a rod shape. When the supporting member 160 is inserted into the installation groove 146, the supporting member 160 may be connected to the base 145 through a rotating shaft provided at an end of the supporting member 160.

The base 145 may rotate in a clockwise or counterclockwise direction with respect to the rotating shaft of the supporting member 160 inserted into the installation groove 146. The installation groove 146 may have a fan shape so that the base 145 can rotate. A central angle of the installation groove 146 may be determined according to a desired degree of rotation of the base 145.

As shown in FIGS. 11A and 11B, two supporting members 160 may be inserted into the base 145. In order for the two supporting members 160 to be inserted into the base 145, two installation grooves 146 may be formed in the base 145. FIGS. 11A and 11B shows the two supporting members 160 being inserted into the base 145, however, three or more supporting members may be inserted into the base 145. In this case, three or more may be formed in the base 145 in correspondence to the number of the supporting members.

Referring to FIGS. 12A and 12Ba single supporting member 160 may be inserted into the base 145. According to the embodiments described above, since the installation groove 146 in which the power transmitter 130 is installed is provided along the center of the base 145, when a single supporting member 160 is inserted into the base 145, the installation groove 146 formed in the base 145 may deviate from the center of the base 145.

According to the embodiments described above, by removing the rotating shaft "r" extending outside the base 145, the number of elements configuring the transducer array 141 can increase, which increases an FOV of the ultrasound probe "P".

If the rotating shaft "r" extends outside the base 145, and the supporting members "S" support the rotating shaft "r", a rotational angle of the base 145 may be limited. However, according to the embodiments described above, since the rotational angle of the base 145 is not limited, a scan angle of the transducer array 141 can also increase.

Also, according to the embodiments described above, since both FOV depending on the size of the transducer array 141 and scan angle depending on a rotational angle of the transducer 140 can increase, a 3D volume imaging area that is determined by the FOV and the rotational angle may also increase.

Figure 13A:
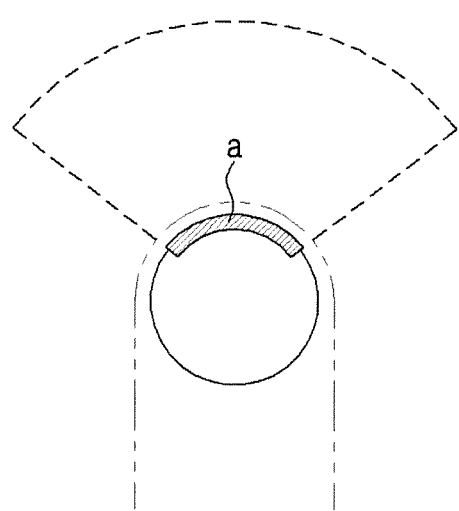
FIGS. 13A and 13B conceptually show a field of view (FOV) and a scan angle of the ultrasound probe of FIG. 7.
Figure 13B:
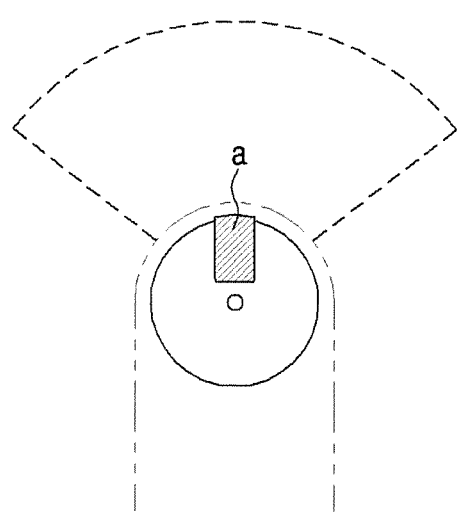
Figure 14:
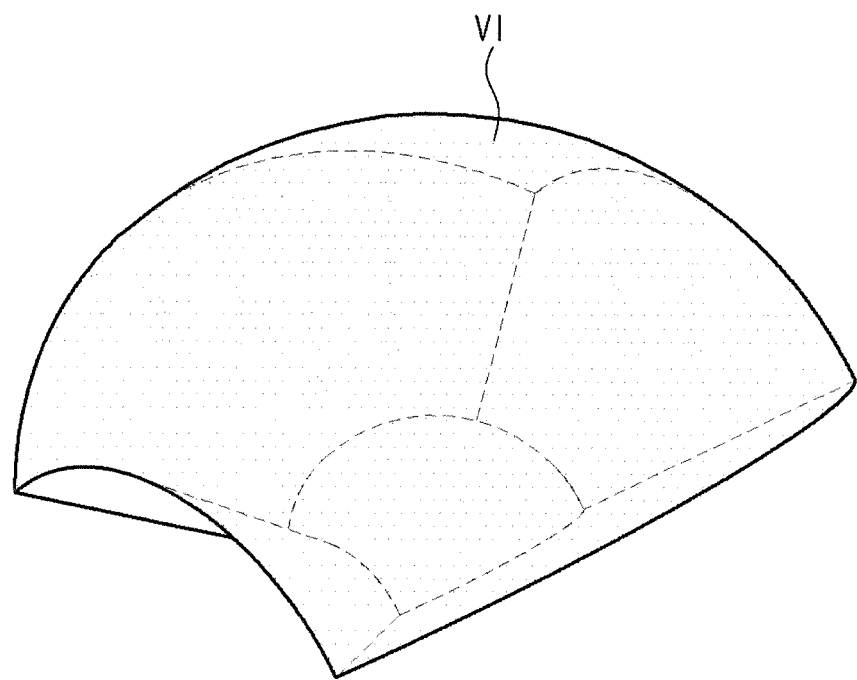
FIG. 14 conceptually shows a 3D imaging area of the ultrasound probe of FIG. 7.
Figure 15A:
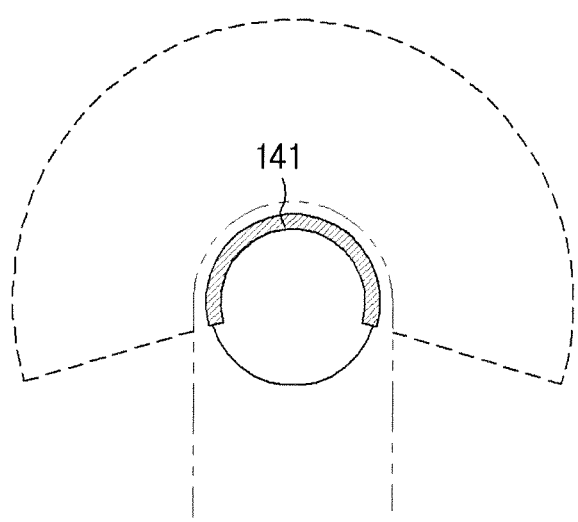
FIGS. 15A and 15B conceptually show an FOV and a scan angle of an ultrasound probe according to an embodiment of the present inventive concept.
Figure 15B:
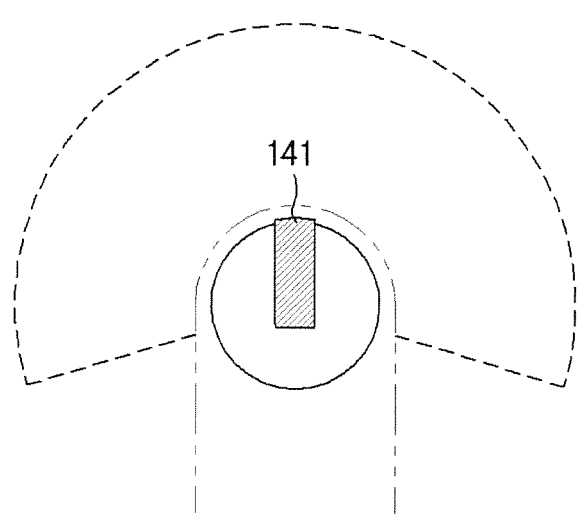
Figure 16:
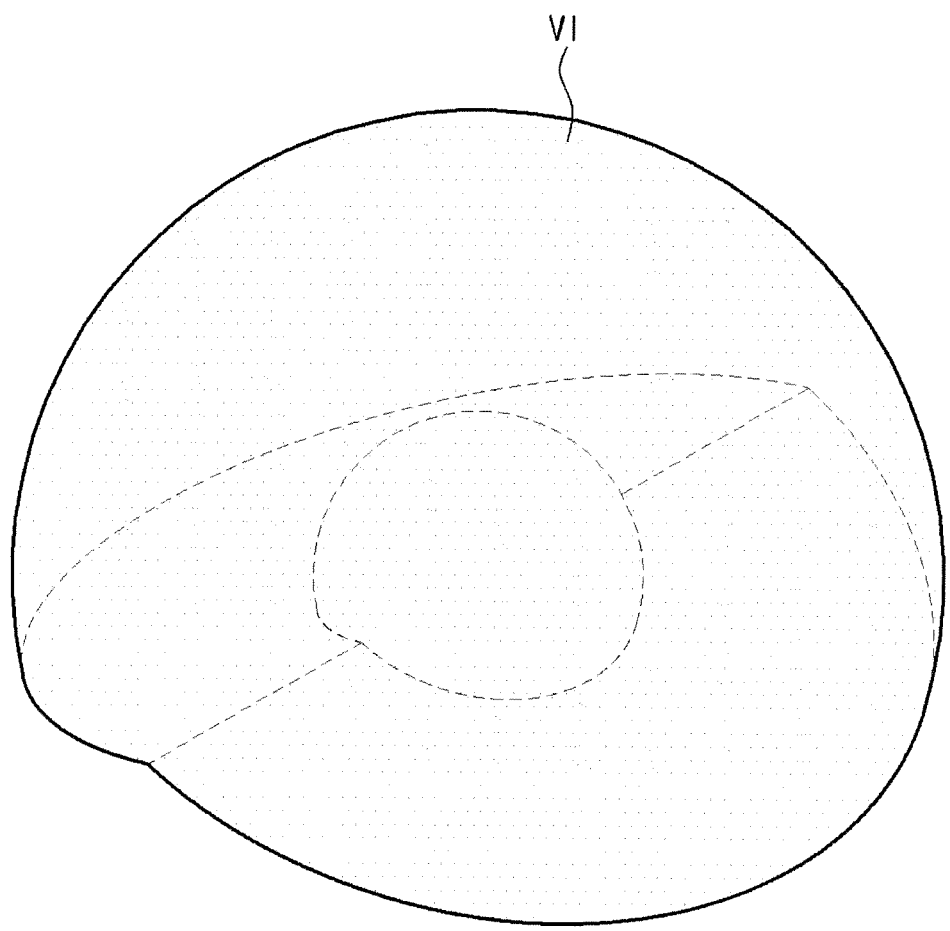
FIG. 16 conceptually shows a 3D imaging area of an ultrasound probe according to an embodiment of the present inventive concept.

FIGS. 13A and 13B conceptually show an FOV and a scan angle of the ultrasound probe "P" of FIGS. 7A and 7B, respectively, FIG. 14 conceptually shows a 3D imaging area of the ultrasound probe "P" of FIGS. 7A and 7B, FIGS. 15A and 15B conceptually show an FOV and a scan angle of the ultrasound probe "P" according to an embodiment of the present inventive concept, and FIG. 16 conceptually shows a 3D imaging area of the ultrasound probe "P" according to an embodiment of the present inventive concept.

If the rotating shaft "r" extends outside the base 145, the transducer array size "a" may be limited by the rotating shaft "r", and the rotational angle of the transducer 140 may also be limited. However, in the ultrasound probe "P" according to the embodiments described above, the size of the transducer array 141 and the rotational angle of the transducer 140 may increase compared to when the rotating shaft "r" extends outside the base 145. Accordingly, as shown in FIGS. 13A to 15B, the FOV and the scan angle of the ultrasound probe "P" according to the embodiments described above may increase compared to when the rotating shaft "r" extends outside the base 145.

Referring to FIGS. 14 and 16, a 3D imaging area VI (see FIG. 16) of the ultrasound probe "P" according to the embodiments is larger than a 3D imaging area VI (see FIG. 14) of when the rotating shaft "r" extends outside the base 145.

As described above, the ultrasound probe according to the present disclosure can provide an improved FOV.

In addition, the rotational angle of the transducer can increase, which leads to a wider 3D imaging area.

Although the exemplary embodiments of the present inventive concept have been shown and described, it would be appreciated by those skilled in the art that changes may be made in these embodiments without departing from the principles and spirit of the disclosure, the scope of which is defined in the claims and their equivalents.

What is claimed is:

1. An ultrasound probe comprising:
   a transducer comprising:
   a spherical base; and
   a transducer array, which is disposed on the base, rotating by rotation of the base at a predetermined angle with a rotating axis extending outwards from a center of the base; and
   a support in contact with an outer surface of the base, on which the transducer is disposed so that the transducer rotates on the support,
   wherein the support includes a rotation guide which supports the base and guides the rotation of the base,
   wherein the rotation guide is in contact with the outer surface of the base,
   wherein the rotating axis and the support are spaced apart from each other, and
   wherein the transducer array is disposed along the outer surface of the base and arranged in a curved shape to have a field of view (FOV) of greater than 180 degrees about an axis perpendicular to the rotating axis.

2. The ultrasound probe according to claim 1, wherein the rotation guide comprises a roller or a bearing which is in contact with the base.

3. The ultrasound probe according to claim 1, further comprising a wire member transferring, a power to the transducer for the rotation thereof.

4. The ultrasound probe according to claim 1, wherein the base includes:
   two or more protrusions along an outer circumferential surface of the base; and
   a groove between the two or more protrusions along the outer circumferential surface of the base, and
   wherein the rotation guide is in contact with a contact surface of the base located adjacent to each of the two or more protrusions.

5. The ultrasound probe according to claim 1, wherein the transducer array extends perpendicular to a direction in which the transducer rotates.

6. The ultrasound probe according to claim 1, wherein the transducer has a rotational angle of 180 degrees or more.

7. The ultrasound probe according to claim 1, further comprising a housing covering the transducer and a driver which generates a power and which is connected with a power transmitter,
   wherein the power transmitter transfers the power to the transducer and includes a power transfer pulley, a wire member, a first guide pulley, and a second guide pulley.

8. The ultrasound probe according to claim 7, wherein the wire member has one end connected to the power transfer pulley and another end connected to the transducer.

9. An ultrasound probe comprising:
   a transducer comprising:
   a globe shaped spherical base; and
   a transducer array, which is disposed on the base, rotating by rotation of the base at a predetermined angle with a rotating axis extending outwards from a center of the base; and
   at least one support having a rod shape, the at least one support being inserted into the transducer to support the transducer and coupled with the transducer on the rotating axis of the transducer,
   wherein the transducer array is disposed along the outer surface of the base and arranged in a curved shape to have a field of view (FOV) of greater than 180 degrees about an axis perpendicular to the rotating axis.

10. The ultrasound probe according to claim 9, wherein the transducer includes at least one groove into which the at least one support is inserted.

11. The ultrasound probe according to claim 10, wherein the at least one groove has a central angle of 180 degrees or more.

12. The ultrasound probe according to claim 9, further comprising a wire member transferring a power to the transducer for rotation thereof,
wherein the base includes:
two or more protrusions along an outer circumferential surface of the base; and
a groove, in which the wire member is inserted, between the two or more protrusions along the outer circumferential surface of the base.

13. The ultrasound probe according to claim 9, wherein the transducer array extends perpendicular to a direction in which the transducer rotates.

14. The ultrasound probe according to claim 9, wherein the transducer has a rotational angle of 180 degrees or more.

15. An ultrasound diagnostic imaging system comprising:
an ultrasound probe transmitting ultrasonic waves to an object, receiving ultrasonic waves reflected from the object, and converting the reflected ultrasonic waves into electrical signals; and
a main body connected to the ultrasound probe through a cable and including an input and a display,
wherein the ultrasound probe includes:
a transducer comprising:
a spherical base; and
a transducer array, which is disposed on the base, rotating by rotation of the base at a predetermined angle with a rotating axis extending outwards from a center of the base; and
a support in contact with an outer surface of the base, on which the transducer is disposed so that the transducer rotates on the support,
wherein the rotating axis and the support are spaced apart from each other,
wherein the support includes a rotation guide which supports the base and guides the rotation of the base,
wherein the rotation guide is in contact with the outer surface of the base, and
wherein the transducer array is disposed along the outer surface of the base and arranged in a curved shape to have a field of view (FOV) of greater than 180 degrees about an axis perpendicular to the rotating axis.

16. The ultrasound probe according to claim 15, wherein the ultrasound probe further includes a wire member transferring a power the transducer for the rotation thereof,
wherein the transducer includes a groove in which the wire member is inserted.

17. The ultrasound probe according to claim 15, wherein the base includes:
two or more protrusions along an outer circumferential surface of the base; and
a groove between the two or more protrusions along the outer circumferential surface of the base,
wherein the rotation guide guides the rotation of the base and is in contact with a contact surface of the base located adjacent to each of the two or more protrusions.

* * * * *